United States Patent [19]
DeSantis, Jr.

[11] Patent Number: 5,288,759
[45] Date of Patent: Feb. 22, 1994

[54] USE OF CERTAIN SULFAMOYL-SUBSTITUTED PHENETHYLAMINE DERIVATIVES TO REVERSE DRUG-INDUCED MYDRIASIS

[75] Inventor: Louis DeSantis, Jr., Fort Worth, Tex.

[73] Assignee: Alcon Laboratories, Inc., Fort Worth, Tex.

[21] Appl. No.: 936,436

[22] Filed: Aug. 27, 1992

[51] Int. Cl.$^5$ ............................................. A61K 31/18
[52] U.S. Cl. ..................................... 514/603; 514/912
[58] Field of Search ................................. 514/912, 603

[56] References Cited

U.S. PATENT DOCUMENTS

| | | | |
|---|---|---|---|
| 4,252,721 | 2/1981 | Silvestrini et al. | 540/578 |
| 4,373,106 | 2/1983 | Imai et al. | 564/85 |
| 4,588,156 | 12/1985 | Imai et al. | 248/243 |
| 4,703,063 | 10/1987 | Imai et al. | 514/603 |
| 4,731,478 | 3/1988 | Niigata et al. | 564/86 |
| 4,761,500 | 8/1988 | Niigata et al. | 564/86 |
| 4,868,216 | 9/1989 | Imai et al. | 514/603 |
| 4,987,152 | 1/1991 | Imai et al. | 514/603 |

FOREIGN PATENT DOCUMENTS

| | | |
|---|---|---|
| 1282077 | 3/1991 | Canada . |
| 0257787B1 | 4/1991 | European Pat. Off. . |

OTHER PUBLICATIONS

"The pharmacological basis of therapeutics" (4th edition) p. 406 (1970).

*Primary Examiner*—Thurman K. Page
*Assistant Examiner*—Jyothsna Venkat
*Attorney, Agent, or Firm*—Julie J. L. Cheng

[57] ABSTRACT

Certain sulfamoyl-substituted phenethylamine derivatives have been found to be useful in reversing or inhibiting drug-induced mydriasis. This application is especially useful in the area of diagnostics for eye examinations.

4 Claims, No Drawings

USE OF CERTAIN SULFAMOYL-SUBSTITUTED PHENETHYLAMINE DERIVATIVES TO REVERSE DRUG-INDUCED MYDRIASIS

BACKGROUND OF THE INVENTION

The present invention relates to the field of ophthalmology. In particular, the present invention relates to diagnostics useful in eye examinations.

During the course of a typical eye examination, the patient's pupils are dilated so that the posterior tissues of the eye can be examined. In general, alpha-1 adrenergic agonists, such as phenylephrine, are used to dilate the pupil (induce mydriasis); however, residual mydriasis after the eye examination may interfere with patient functioning and is undesirable. In addition, the drug-induced mydriasis may precipitate an attack of angle closure glaucoma in susceptible individuals.

The mydriatic action of phenylephrine and other alpha-1 agonists may be competitively inhibited or reversed by using alpha-1 adrenergic antagonists. The most widely used agent to date has been dapiprazole; however, there are several disadvantages to using dapiprazole. Due to its instability in solution, the dapiprazole product is supplied in three parts (drug and excipient ingredients) which require reconstitution by a qualified individual prior to use. This reconstituted product has a very limited shelf life (on the average 21 days). The product causes discomfort in the eye and has been known to cause side effects, such as burning, lid edema, chemosis, browache, headaches, and itching, in a large number of patients. Moreover, multiple instillations must be administered in order to achieve the desired effect.

SUMMARY OF THE INVENTION

It has now been found that certain sulfamoyl-substituted phenethylamine derivatives are useful in inhibiting or reversing the drug-induced mydriasis without the disadvantages of dapiprazole. These compounds are more potent than dapiprazole, are comfortable upon instillation to the eye and are stable in solution, with a relatively long shelf life.

DETAILED DESCRIPTION OF THE INVENTION

The sulfamoyl-substituted phenethylamine derivatives useful in the present invention are disclosed in U.S. Pat. No. 4,373,106 (Imai, et al.) and U.S. Pat. No. 4,731,478 (Niigata, et al.). These patents also disclose processes for producing these compounds. The general structure of these compounds is shown in Structure (I), below:

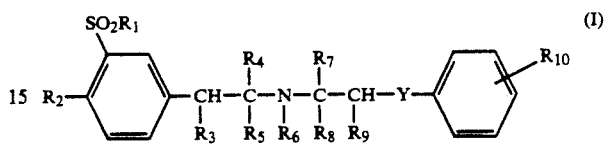

and acid addition salts thereof, wherein $R_1$ represents an amino group or a mono- or di-lower alkylamino group; $R_2$ represents a hydroxyl group, a lower alkyl group, or a lower alkoxy group; $R_3$ represents hydrogen, halogen, a lower alkyl group, a lower alkoxy group, a phenylthio group, or a phenylsulfinyl group; $R_4$, $R_5$, $R_6$, $R_7$, $R_8$ and $R_9$ are selected independently from hydrogen and lower alkyl groups; $R_{10}$ represents hydrogen, a lower alkyl group, or a lower alkoxy group; and Y represents oxygen or a methylene group and is oxygen when $R_2$ is a hydroxyl group.

The term "lower" used herein means a straight or branched carbon chain having 1 to 5 carbon atoms. For example, "lower alkyl group" includes methyl, ethyl, propyl, butyl, pentyl and isobutyl groups, etc.; and "lower alkoxy group" includes methoxy, ethoxy, propoxy and butoxy groups, etc. In addition, in the above-described formula, $R_{10}$ which is a substituent of the benzene ring may be disposed at any position ortho-, meta or para-to the side chain. Furthermore, since the compounds of this invention shown by Structure (I) can readily form salts and contain asymmetric carbon atom(s), the invention includes the salts thereof, and any optically active or inactive isomer or isomer mixture thereof. The preferred compounds, Structure (II), are listed in the following Table 1:

TABLE 1

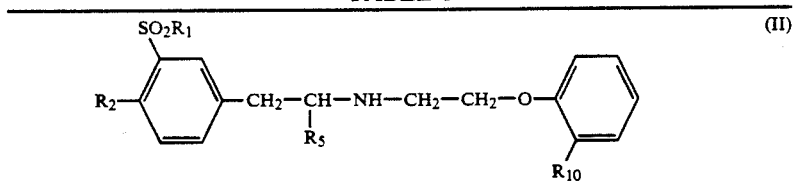

| COMPOUND | | $R_1$ | $R_2$ | $R_5$ | $R_{10}$ |
|---|---|---|---|---|---|
| A. | 2-methoxy-5-[2-[2-(2-methoxy-phenoxy)ethylamino]-2-methylethyl]-N-methylbenzenesulfonamide hydrochloride | NHCH$_3$ | CH$_3$O | CH$_3$ | OCH$_3$ |
| B. | 2-methoxy-5-[2-[2-(2-methoxy-phenoxy)ethylamino]-2-methylethyl]-N,N-dimethylbenzenesulfonamide hydrochloride | N(CH$_3$)$_2$ | CH$_3$O | CH$_3$ | OCH$_3$ |
| C. | 2-methoxy-5-[2-[2-(2-methoxy-phenoxy)ethylamino]ethyl]benzene-sulfonamide hydrochloride | NH$_2$ | CH$_3$O | H | OCH$_3$ |
| D. | 5-[2-[2-(2-methoxyphenoxy)-ethylamino]ethyl]-2-methylbenzene-sulfonamide hydrochloride | NH$_2$ | CH$_3$ | H | OCH$_3$ |
| E. | 5-[2-[2-(2-ethoxyphenoxy)-ethylamino]ethyl]-2-methylbenzene-sulfonamide hydrochloride | NH$_2$ | CH$_3$ | H | OCH$_2$CH$_3$ |
| F. | 2-hydroxy-5-[2-[2-(2-methoxy-phenoxy)ethylamino]ethyl]benzene-sulfonamide | NH$_2$ | HO | H | OCH$_3$ |

TABLE 1-continued $$\text{R}_2\underset{\underset{\text{R}_5}{|}}{\overset{SO_2R_1}{\bigcirc}}-CH_2-CH-NH-CH_2-CH_2-O-\underset{R_{10}}{\bigcirc} \qquad (II)$$

| COMPOUND | $R_1$ | $R_2$ | $R_5$ | $R_{10}$ |
| --- | --- | --- | --- | --- |
| sulfonamide | | | | |
| G. 2-methoxy-5-[2-[2-(2-methoxyphenoxy)ethylamino]-2-methylethyl]benzenesulfonamide hydrochloride | $NH_2$ | $CH_3O$ | $CH_3$ | $OCH_3$ |
| H. 5-[2-[2-(2-ethoxyphenoxy)-ethylamino]-2-methylethyl]-2-methoxybenzenesulfonamide hydrochloride | $NH_2$ | $CH_3O$ | $CH_3$ | $OCH_2CH_3$ |
| I. 5-[2-[2-(2-methoxyphenoxy)-ethylamino]-2-methylethyl]-2-methylbenzenesulfonamide hydrochloride | $NH_2$ | $CH_3$ | $CH_3$ | $OCH_3$ |
| K. 5-[2-[2-(2-methoxyphenoxy)-ethylamino]-2-ethylethyl]-2-methylbenzenesulfonamide hydrochloride | $NH_2$ | $CH_3$ | $CH_2CH_3$ | $OCH_3$ |

Especially preferred is S-(-)-5-[2-[2-(2-ethoxyphenoxy)-ethylamino]-2-methylethyl]-2-methoxybenzenesulfonamide hydrochloride, which is also known as amsulosin.

As the processes for preparing the compounds of Structure (I) are described in detail in U.S. Pat. No. 4,731,478 (and related patents), the preparation procedures will not be detailed herein. The entire contents of the above-referenced patent is incorporated herein by reference.

In general, the compounds of the present invention are administered topically in aqueous compositions so that one or two drops of such a composition will provide a dose of between about 0.6 and about 600 micrograms ($\mu$g) of the compound, preferably between about 6 and 60 $\mu$g. These compositions will typically be instilled once or twice in a patient's eye when needed to terminate mydriasis.

EXAMPLE 1

The following is an example of a preferred composition of the present invention.

TABLE 2

| INGREDIENT | CONCENTRATION (w/v%) |
| --- | --- |
| Amsulosin | 0.545* |
| Hydroxypropyl Methyl Cellulose (2910) (E4M) | 0.5 |
| Monobasic Sodium Phosphate.1H$_2$O | 0.05 |
| Dibasic Sodium Phosphate (Anhydrous) | 0.15 |
| Sodium Chloride | 0.75 |
| Mannitol | 2.0 |
| Disodium EDTA | 0.01 |
| Benzalkonium Chloride | 0.01 + 5% xs |
| NaOH and/or HCl | q.s. to pH 6.6 |
| Purified Water | q.s. to 100 |

*Equivalent to 0.5% of the free base.

Preparation:

Amsulosin, hydroxypropyl methyl cellulose (HPMC), sodium phosphate, sodium chloride, mannitol, EDTA and benzalkonium chloride (BAC) were dissolved in about 90% of the total volume of water. The pH was then adjusted to 6.6 by the addition of NaOH/HCl. Last, volume was brought to 100% by the addition of water.

EXAMPLE 2

The following study was conducted to determine the effect of a drop of dapiprazole versus one drop of amsulosin on phenylephrine-induced mydriasis in New Zealand Albino (NZA) rabbits.

Mydriasis was induced in New Zealand albino rabbits using topical ocular instillation of a single 30 microliter drop containing 3 milligrams of phenylephrine (10% Neo-Synephrine hydrochloride). One hour later, drops of either dapiprazole solution or amsulosin solution were administered and the pupil diameter was measured at 0.5, 1, 1.5 2, 3 and 4 hours post-dose. The percentage change from baseline (pre-phenylephrine) of pupil diameter was calculated for each time point. In some experiments, dapiprazole and amsulosin were given in two divided doses, each consisting of two 30 microliter drops, at an interval of 5 minutes. Control eyes were given saline solution in place of amsulosin or dapiprazole. In other experiments, a single drop of amsulosin or dapiprazole was given at one hour after phenylephrine. This protocol was designed to investigate the dose-response relationship for dapiprazole and amsulosin for reversing phenylephrine-induced mydriasis after single and multiple drop instillation. The recommended clinical dosage for 0.5% dapiprazole hydrochloride ophthalmic solution is topically, 2 drops followed 5 minutes later by an additional 2 drops in the conjunctiva following the ophthalmic examination to reverse the diagnostic mydriasis.

TABLE 3

| TEST COMPOUND(S) | Time (hr) | Pupil Diameter (mm) | % Change |
| --- | --- | --- | --- |
| Phenylephrine (3 mg) + | −1.0 | 5.9 | 0.0 |
| Dapiprazole (150 $\mu$g) | 0.0 | 8.5 | 43.5 |
| | 0.5 | 5.6 | −5.3 |
| | 1.0 | 5.5 | −7.8 |
| | 1.5 | 5.8 | −2.2 |
| | 2.0 | 5.9 | −1.0 |
| | 3.0 | 5.9 | 0.2 |
| | 4.0 | 6.0 | 0.8 |
| Phenylephrine (3 mg) + | −1.0 | 5.7 | 0.0 |
| Amsulosin (150 $\mu$g) | 0.0 | 8.1 | 42.0 |

TABLE 3-continued

| TEST COMPOUND(S) | Time (hr) | Pupil Diameter (mm) | % Change |
|---|---|---|---|
|  | 0.5 | 5.6 | −1.6 |
|  | 1.0 | 5.5 | −2.7 |
|  | 1.5 | 5.5 | −2.7 |
|  | 2.0 | 5.5 | −2.8 |
|  | 3.0 | 5.4 | −5.8 |
|  | 4.0 | 5.6 | −2.1 |
| Phenylephrine (3 mg) + | −1.0 | 6.1 | 0.0 |
| Dapiprazole (15 μg) | 0.0 | 8.7 | 43.8 |
|  | 0.5 | 7.4 | 23.2 |
|  | 1.0 | 7.6 | 26.3 |
|  | 1.5 | 7.4 | 21.9 |
|  | 2.0 | 7.3 | 20.5 |
|  | 3.0 | 6.7 | 11.2 |
|  | 4.0 | 6.5 | 6.8 |
| Phenylephrine (3 mg) + | −1.0 | 5.5 | 0.0 |
| Amsulosin (15 μg) | 0.0 | 8.6 | 57.4 |
|  | 0.5 | 5.5 | 1.4 |
|  | 1.0 | 5.4 | −0.7 |
|  | 1.5 | 5.4 | −0.9 |
|  | 2.0 | 5.2 | −4.2 |
|  | 3.0 | 5.3 | −3.6 |
|  | 4.0 | 5.4 | −1.4 |
| Phenylephrine (3 mg) + | −1.0 | 5.8 | 0.0 |
| Vehicle | 0.0 | 8.7 | 51.1 |
|  | 0.5 | 8.8 | 53.1 |
|  | 1.0 | 8.4 | 44.7 |
|  | 1.5 | 8.0 | 39.2 |
|  | 2.0 | 7.6 | 31.1 |
|  | 3.0 | 7.0 | 20.5 |
|  | 4.0 | 6.8 | 16.9 |

The results, shown in Table 3, above indicate that one 15 μg drop of amsulosin was as effective as one 150 μg drop of dapiprazole in reversing phenylephrine-induced mydriasis in NZA rabbits; however, one drop of 15 μg dapiprazole failed to reverse completely the phenylephrine effect. Thus, amsulosin is much more potent than dapiprazole for reversing phenylephrine-induced mydriasis. Furthermore, these results demonstrate that amsulosin is effective when given as a single drop, as opposed to the multiple drops required for dapiprazole.

The results also indicate that amsulosin has a longer duration of effect than dapiprazole. At the 150 jig dose level, the pupil diameter was less than baseline at 0.5, 1 and 1.5 hours after dosing with dapiprazole; on the other hand, the pupil diameter was below baseline at 0.5 through 4 hours after amsulosin. This indicates that the effect of amsulosin may outlast that of dapiprazole at this dosage.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for reversing or inhibiting drug-induced mydriasis by the topical application to an affected eye a composition comprising an ophthalmically acceptable carrier and a mydriasis-inhibiting amount of a compound selected from the racemic and enantiomeric forms and acid addition salts of 5-[2-[2-(2-ethoxyphenoxy)-ethylamino]-2-methylethyl]-2-methoxybenzenesulfonamide.

2. The method of claim 1, wherein the compound comprises the (-) isomer and acid addition salts of 5-[2-[2-(2-ethoxyphenoxy)ethylamino]-2-methyl-ethyl]-2-methoxybenzenesulfonamide.

3. The method of claim 1, wherein between about 0.6 and about 600 micrograms of said compound is administered.

4. The method of claim 3, wherein between about 6 and 60 micrograms of said compound is administered.

* * * * *

UNITED STATES PATENT AND TRADEMARK OFFICE
CERTIFICATE OF CORRECTION

PATENT NO. : 5,288,759
DATED : February 22, 1994
INVENTOR(S) : Louis DeSantis, Jr It is certified that error appears in the above-indentified patent and that said Letters Patent is hereby corrected as shown below:

Column 6, line 4, change "150 jig" to --150 µg--.

Signed and Sealed this

Twenty-fifth Day of October, 1994

Attest:

BRUCE LEHMAN

*Attesting Officer*    *Commissioner of Patents and Trademarks*